US009345625B2

(12) United States Patent
LaVon et al.

(10) Patent No.: US 9,345,625 B2
(45) Date of Patent: May 24, 2016

(54) METHOD OF MAKING PREFASTENED REFASTENABLE DISPOSABLE ABSORBENT ARTICLES (71) Applicant: The Procter & Gamble Company, Cincinnati, OH (US)

(72) Inventors: Gary Dean LaVon, Liberty Township, OH (US); Joseph Hung Lam, Mason, OH (US); Kazuaki Tameishi, Akashi (JP); Koichi Morimoto, Beijing (CN); Yoichiro Yamamoto, Cologne (DE); Norman Gorospe Juguilon, Tresalveo (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/575,147

(22) Filed: Dec. 18, 2014

(65) Prior Publication Data
US 2015/0101739 A1    Apr. 16, 2015

Related U.S. Application Data (62) Division of application No. 13/221,127, filed on Aug. 30, 2011, now Pat. No. 8,945,326.

(60) Provisional application No. 61/382,590, filed on Sep. 14, 2010.

(51) Int. Cl.
*A61F 13/15*   (2006.01)
*A61F 13/496*  (2006.01)

(52) U.S. Cl.
CPC ..... *A61F 13/15699* (2013.01); *A61F 13/15593* (2013.01); *A61F 13/15756* (2013.01); *A61F 13/15764* (2013.01); *A61F 13/496* (2013.01); *Y10T 156/1015* (2015.01); *Y10T 156/1044* (2015.01); *Y10T 156/1049* (2015.01);
(Continued)

(58) Field of Classification Search
None
See application file for complete search history.

(56) References Cited

U.S. PATENT DOCUMENTS 3,772,120 A   11/1973  Radzins
3,848,594 A   11/1974  Buell
(Continued)

FOREIGN PATENT DOCUMENTS

JP    1995080023 A    3/1995
WO    WO 00/37010 A1  6/2000

OTHER PUBLICATIONS

PCT International Search Report dated Nov. 22, 2011, 11 pages.

*Primary Examiner* — Barbara J Musser
(74) *Attorney, Agent, or Firm* — Charles R. Matson (57) ABSTRACT The present disclosure relates to methods for manufacturing absorbent articles, and in particular, methods for making pre-fastened refastenable pant diapers. Aspects of the methods according to the present disclosure relate to the fabrication of refastenable pant diapers wherein discrete chassis are advanced in a machine direction such that the lateral axis is parallel with the machine direction. First side panels are then refastenably connected with the first waist region, and second side panels are permanently connected the second waist regions of the discrete chassis. The chassis are connected with discrete lengths of side panel material and/or connection zone material. The chassis are then folded, and the first and second side panels are subsequently bonded together. The article is then subjected to knife cut at or adjacent the bonded regions to create discrete, pre-fastened refastenable pant diapers.

8 Claims, 8 Drawing Sheets (52) U.S. Cl.
CPC ...... *Y10T156/1051* (2015.01); *Y10T 156/1074* (2015.01); *Y10T 156/1075* (2015.01); *Y10T 156/1084* (2015.01)

(56) References Cited

U.S. PATENT DOCUMENTS

| | | | |
|---|---|---|---|
| 3,860,003 A | 1/1975 | Buell | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,735,673 A | 4/1988 | Piron | |
| 4,775,375 A | 10/1988 | Aledo | |
| 4,795,454 A | 1/1989 | Dragoo | |
| 4,834,735 A | 5/1989 | Alemany et al. | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,940,464 A | 7/1990 | Van Gompel | |
| 4,946,527 A | 8/1990 | Battrell | |
| 4,950,264 A | 8/1990 | Osborn | |
| 5,092,861 A | 3/1992 | Nomura | |
| 5,151,092 A | 9/1992 | Buell et al. | |
| 5,221,274 A | 6/1993 | Buell et al. | |
| 5,246,433 A | 9/1993 | Hasse | |
| 5,366,782 A | 11/1994 | Curro | |
| 5,429,694 A | 7/1995 | Herrmann | |
| 5,518,801 A | 5/1996 | Chappell et al. | |
| 5,562,646 A | 10/1996 | Goldman et al. | |
| 5,569,234 A | 10/1996 | Buell | |
| 5,599,335 A | 2/1997 | Goldman et al. | |
| 5,607,537 A | 3/1997 | Johnson et al. | |
| 5,622,589 A | 4/1997 | Johnson et al. | |
| 5,628,097 A | 5/1997 | Benson et al. | |
| 5,662,638 A | 9/1997 | Johnson et al. | |
| 5,669,894 A | 9/1997 | Goldman et al. | |
| 5,691,035 A | 11/1997 | Chappell et al. | |
| 5,702,551 A | 12/1997 | Huber et al. | |
| 5,723,087 A | 3/1998 | Chappell et al. | |
| 5,735,840 A | 4/1998 | Kline et al. | |
| 5,772,825 A | 6/1998 | Schmitz | |
| 5,779,831 A | 7/1998 | Schmitz | |
| 5,891,544 A | 4/1999 | Chappell et al. | |
| 5,897,545 A | 4/1999 | Kline | |
| 5,916,661 A | 6/1999 | Benson et al. | |
| 5,928,212 A | 7/1999 | Kline et al. | |
| 5,957,908 A | 9/1999 | Kline | |
| 5,968,029 A | 10/1999 | Chappell et al. | |
| 5,993,432 A | 11/1999 | Lodge et al. | |
| 6,017,406 A | 1/2000 | Vogt | |
| 6,042,673 A | 3/2000 | Johnson et al. | |
| 6,107,539 A | 8/2000 | Palumbo et al. | |
| 6,113,717 A | 9/2000 | Vogt et al. | |
| 6,120,487 A | 9/2000 | Ashton | |
| 6,120,489 A | 9/2000 | Johnson | |
| 6,251,097 B1 | 6/2001 | Kline et al. | |
| 6,352,607 B1 | 3/2002 | Kuen et al. | |
| 6,432,098 B1 | 8/2002 | Kline et al. | |
| 6,497,032 B2 | 12/2002 | Maxton et al. | |
| 6,545,197 B1 | 4/2003 | Muller et al. | |
| 6,546,987 B1 | 4/2003 | Tachibana et al. | |
| 6,596,107 B2 | 7/2003 | Stopher | |
| 6,620,276 B1 | 9/2003 | Kuntze et al. | |
| 6,648,869 B1 | 11/2003 | Gillies et al. | |
| 6,669,618 B2 | 12/2003 | Reising et al. | |
| 6,723,035 B2 | 4/2004 | Franklin et al. | |
| 6,726,792 B1 | 4/2004 | Johnson et al. | |
| 6,755,809 B2 | 6/2004 | Kline et al. | |
| 6,776,316 B2 | 8/2004 | Van Eperen et al. | |
| 6,790,798 B1 | 9/2004 | Suzuki et al. | |
| 6,811,019 B2 | 11/2004 | Christian et al. | |
| 6,830,800 B2 | 12/2004 | Curro et al. | |
| 6,913,664 B2 | 7/2005 | Umebayashi et al. | |
| 6,915,829 B2 | 7/2005 | Popp et al. | |
| 6,962,578 B1 | 11/2005 | LaVon | |
| 7,172,585 B2 | 2/2007 | Sandin et al. | |
| 7,270,861 B2 | 9/2007 | Broering et al. | |
| 7,341,579 B2 | 3/2008 | Kinoshita | |
| 7,361,167 B2 | 4/2008 | Erickson et al. | |
| 7,383,865 B2 | 6/2008 | Umebayashi et al. | |
| 7,390,373 B2 | 6/2008 | Karlsson et al. | |
| 7,569,039 B2 | 8/2009 | Matsuda et al. | |
| 7,587,966 B2 | 9/2009 | Nakakado et al. | |
| 7,799,006 B2 | 9/2010 | Kline | |
| 7,828,783 B2 | 11/2010 | Erickson et al. | |
| 7,975,584 B2 | 7/2011 | McCabe | |
| 2002/0002358 A1 | 1/2002 | Durrance et al. | |
| 2002/0119878 A1 | 8/2002 | Stopher | |
| 2002/0148557 A1 | 10/2002 | Heller et al. | |
| 2002/0151422 A1 | 10/2002 | Duhm et al. | |
| 2003/0088220 A1 | 5/2003 | Molander | |
| 2003/0131943 A1 | 7/2003 | Frederisy | |
| 2003/0205312 A1 | 11/2003 | Tomsovic et al. | |
| 2003/0233082 A1 | 12/2003 | Kline | |
| 2004/0030318 A1 | 2/2004 | Karlsson et al. | |
| 2004/0089403 A1 | 5/2004 | Satoh | |
| 2004/0097895 A1 | 5/2004 | Busam et al. | |
| 2004/0138635 A1 | 7/2004 | Sorenson et al. | |
| 2004/0158212 A1 | 8/2004 | Ponomarenko et al. | |
| 2004/0243083 A1 | 12/2004 | Matsuda et al. | |
| 2005/0107764 A1 | 5/2005 | Matsuda et al. | |
| 2005/0130821 A1 | 6/2005 | Reising | |
| 2005/0215970 A1 | 9/2005 | Kline | |
| 2005/0215971 A1 | 9/2005 | Roe | |
| 2005/0234419 A1 | 10/2005 | Kline | |
| 2006/0108054 A1 | 5/2006 | Ukegawa | |
| 2006/0244166 A1 | 11/2006 | Wada et al. | |
| 2007/0074381 A1 | 4/2007 | Raycheck | |
| 2007/0078426 A1 | 4/2007 | Kline | |
| 2007/0078427 A1 | 4/2007 | Raycheck et al. | |
| 2007/0093769 A1 | 4/2007 | Kline et al. | |
| 2007/0142808 A1 | 6/2007 | Wada et al. | |
| 2007/0250029 A1 | 10/2007 | Popp et al. | |
| 2008/0083489 A1 | 4/2008 | Schneider et al. | |
| 2008/0084497 A1 | 4/2008 | Sasaki et al. | |
| 2008/0099130 A1 | 5/2008 | Umebayashi et al. | |
| 2008/0107861 A1 | 5/2008 | Dalal | |
| 2008/0208156 A1 | 8/2008 | LaVon | |
| 2008/0234649 A1 | 9/2008 | Hamall | |
| 2009/0094941 A1 | 4/2009 | Burns, Jr. et al. | |
| 2009/0098995 A1 | 4/2009 | Burns, Jr. et al. | |
| 2009/0312730 A1 | 12/2009 | LaVon et al. | |
| 2009/0312732 A1 | 12/2009 | LaVon | |
| 2009/0312735 A1 | 12/2009 | LaVon | |
| 2009/0312737 A1 | 12/2009 | LaVon | |
| 2009/0312738 A1 | 12/2009 | LaVon | |
| 2010/0049155 A1 | 2/2010 | Soderbergh et al. | |

METHOD OF MAKING PREFASTENED REFASTENABLE DISPOSABLE ABSORBENT ARTICLES

CROSS REFERENCE TO RELATED APPLICATION

This application is a divisional of application Ser. No. 13/221,127, filed on Aug. 30, 2011 now U.S. Pat. No. 8,945,326, which claims the benefit of U.S. Provisional Application No. 61/382,590, filed on Sep. 14, 2010, which are all incorporated herein by reference.

FIELD OF THE INVENTION

The present disclosure relates to methods for manufacturing absorbent articles, and more particularly, to methods for making pre-fastened refastenable disposable absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist caps, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chasses are then connected with continuous lengths of elastically extendable front and back belts advancing in the machine direction. While connected with the chassis, the front and back belts are maintained in a fully stretched condition along the machine direction. As such, the positions of the advancing chassis and associated belts can be controlled more easily to allow for more accurate registration and phasing of subsequent converting operations, such as folding, seaming, and cutting. However, introducing discrete elastically extendable components in one or both of the waist regions presents a different challenge with regard to maintaining control and positioning of the advancing discrete elastically extendable components relative to other components, such as an article chassis, can be difficult. For example, when manufacturing refastenable diaper pants with a chassis connected with discrete lengths of elastically extendable panel material disposed in one or both waist regions, some processes utilize a sheet that interconnects the discrete lengths of extendable panel material together during manufacturing, and in turn, enhances the ability to control the advancing components. The sheet is included as part of the manufactured diapers and must be removed by the user before using the refastenable features of the diapers. However, including such a removable sheet on manufactured diaper pants may have a negative impact on costs and aesthetics.

SUMMARY OF THE INVENTION

The present disclosure relates to methods for manufacturing absorbent articles, and in particular, methods for making pre-fastened refastenable pant diapers. Aspects of the methods according to the present disclosure relate to the fabrication of refastenable pant diapers wherein discrete chassis are advanced in a machine direction such that the lateral axis is parallel with the machine direction. First side panels are then refastenably connected with the first waist region, and second side panels are permanently connected the second waist regions of the discrete chassis. The chassis are connected with discrete lengths of side panel material and/or connection zone material, forming a continuous web of articles formed by intermittently spaced chassis and intermittently spaced side panels bridging the gap between the intermittently spaced chassis. The chassis are then folded, and the first and second side panels are subsequently bonded together. The article is then subjected to knife cut at or adjacent the bonded regions to create discrete, pre-fastened refastenable pant diapers.

In one form, a process may be adapted for assembling disposable pre-fastened pant diapers, each pant diaper comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each pant diaper further comprising laterally opposed first side panels refastenably connected with the first waist region; and laterally opposed second side panels permanently connected with the second waist region and permanently connected with corresponding first side panels to form a waist opening. The process includes the steps of: advancing a first continuous web having a first surface and an opposing second surface in a machine direction wherein fastener components are connected with the first surface; cutting the first continuous web into discrete patches, each patch having a leading end region, a trailing end region, and a central region disposed between the leading and trailing end regions, wherein a first fastener is located in the leading end region and a second fastener is located in the trailing end region; advancing a second continuous web in the machine direction; advancing a third continuous web in the machine direction; cutting the third continuous web into discrete chassis, wherein each chassis advances such that the longitudinal axis is parallel with the machine direction; turning each chassis such that the lateral axis is parallel with the machine direction; refastenably connecting the first waist region of each chassis with a trailing end region of a first advancing patch and with a leading end region of a second advancing patch; permanently connecting the second waist region of each chassis with the second continuous web; folding each chassis along the lateral axis to position the central region of each patch into a facing relationship with the second continuous web; bonding a portion of the central region each patch with the second continuous web to create discrete bond regions; and cutting the second continuous web and the patches along the bond regions to create discrete pre-fastened refastenable pant diapers.

In another form, a process may be adapted for assembling disposable pre-fastened pant diapers, each pant diaper comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each pant diaper further comprising laterally opposed first side panels refastenably connected with the first waist region; and laterally opposed second side panels permanently connected with the second waist region and permanently connected with corresponding first side panels to form a waist opening. The process includes the steps of: advancing a first continuous web having a first surface and an opposing second surface in a machine direction wherein fastener components are connected with the first surface; cutting the first continuous web into first discrete patches, each first patch having a leading end region, a trailing end region, and a central region disposed between the leading and trailing end regions, wherein a first fastener is located in the leading end region and a second fastener is located in the trailing end region; advancing a second continuous web in the machine direction; cutting the second continuous web into second discrete patches, each second patch having a leading end region, a trailing end region, and a central region disposed between the leading and trailing end regions, advancing a third continuous web in the machine direction; cutting the third continuous web into discrete chasses, wherein each chassis advances such that the longitudinal axis is parallel with the machine direction; turning each chassis such that the lateral axis is parallel with the machine direction; refastenably connecting the first waist region of each chassis with a trailing end region of an advancing first patch and with a leading end region of a subsequently advancing first patch; permanently connecting the second waist region of each chassis with a trailing end region of an advancing second patch and with a leading end region of a subsequently advancing second patch; folding each chassis along the lateral axis to position the central region of each first patch into a facing relationship with the central region of each second patch; bonding a portion of the central region of each first patch with a portion of each second patch to create discrete bond regions; and cutting the first and second patches along the bond regions to create discrete pre-fastened refastenable pant diapers.

BRIEF DESCRIPTION OF THE DRAWINGS

FIG. 5A is a view of a continuous length of chassis assemblies from FIGS. 3 and 4 taken along line A-A.

FIG. 5B1 is a view of a discrete chassis from FIGS. 3 and 4 taken along line B1-B1.

FIG. 5B2 is a view of a discrete chassis from FIGS. 3 and 4 taken along line B2-B2.

FIG. 5F1 is a view of multiple discrete chassis spaced from each other along the machine direction MD connected with each other by the back side panel material and discrete lengths of front side panel material from FIG. 3 taken along line F1-F1.

FIG. 5F2 is a view of multiple discrete chassis spaced from each other along the machine direction MD connected with each other by the discrete lengths of back side panel material and discrete lengths of front side panel material from FIG. 4 taken along line F2-F2.

DETAILED DESCRIPTION OF THE INVENTION

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils.

These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "preclosed diaper", "diaper-pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in Japanese Patent Publication No. 1995080023A published Mar. 8, 1995.

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods for manufacturing absorbent articles, and in particular, methods for making pre-fastened refastenable pant diapers. As discussed in more detail below, pre-fastened pant diapers may include a chassis having a first waist region and a longitudinally opposed second waist region. The chassis may also include a longitudinal axis and a lateral axis, wherein the longitudinal axis extends through the first and second waist regions. Each pant diaper may further include laterally opposed first side panels refastenably connected with the first waist region, and laterally opposed second side panels permanently connected with the second waist region and permanently connected with corresponding first side panels to form a waist opening. Aspects of the methods according to the present disclosure relate to the fabrication of refastenable pant diapers wherein discrete chassis are advanced in a machine direction such that the lateral axis is parallel with the machine direction. The discrete chassis are also spaced apart from each other along the machine direction. First side panels are then refastenably connected with the first waist region, and second side panels are permanently connected the second waist regions of the discrete chassis. As discussed in more detail below, the methods disclosed herein connect chassis with discrete lengths of side panel material and/or connection zone material and eliminates the need for a removable sheet used in some manufacturing processes. This configuration forms a continuous web of articles formed by intermittently spaced chassis and intermittently spaced side panels bridging the gap between the intermittently spaced chassis. The forces imposed on the continuous web of absorbent articles during manufacture thereby extend through the front side panels and front waist region of the chassis and the back side panels and the back waist region of the chassis. The chassis are then folded in the cross direction parallel to a lateral centerline and the first and second side panels are subsequently bonded together. The article is then subjected to knife cut at or adjacent the bonded regions to create discrete, pre-fastened refastenable pant diapers.

The following provides a general description of various types of pant diapers that may be produced with the methods and apparatuses disclosed herein to help provide additional context to the subsequent discussion of the process embodiments.

Figure 1:
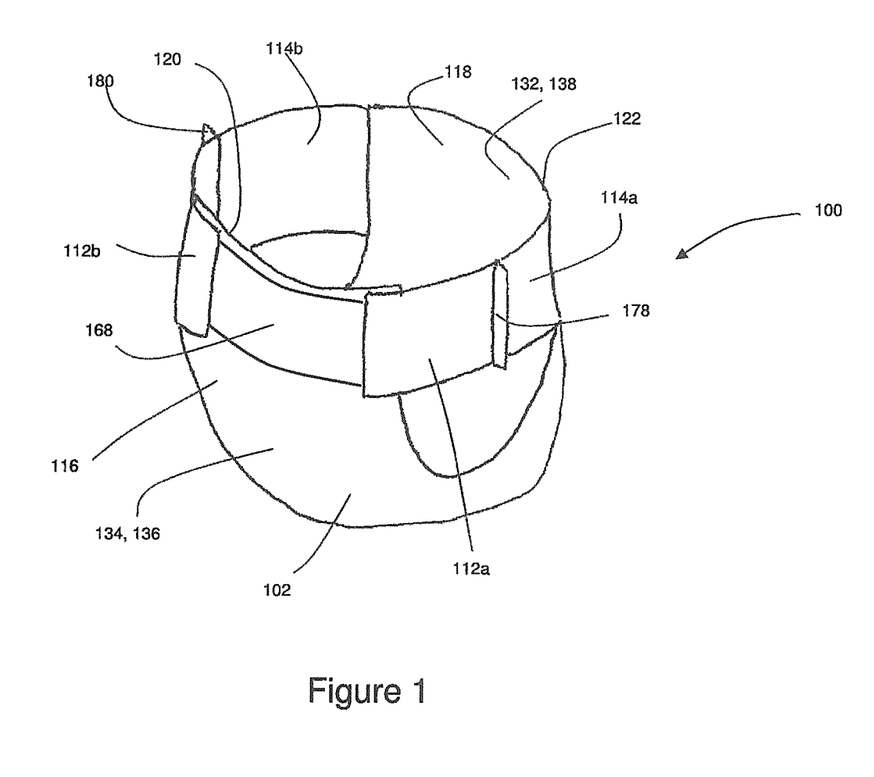
FIG. 1 is a perspective view of a refastenable pant diaper in a pre-fastened configuration.
Figure 2A:
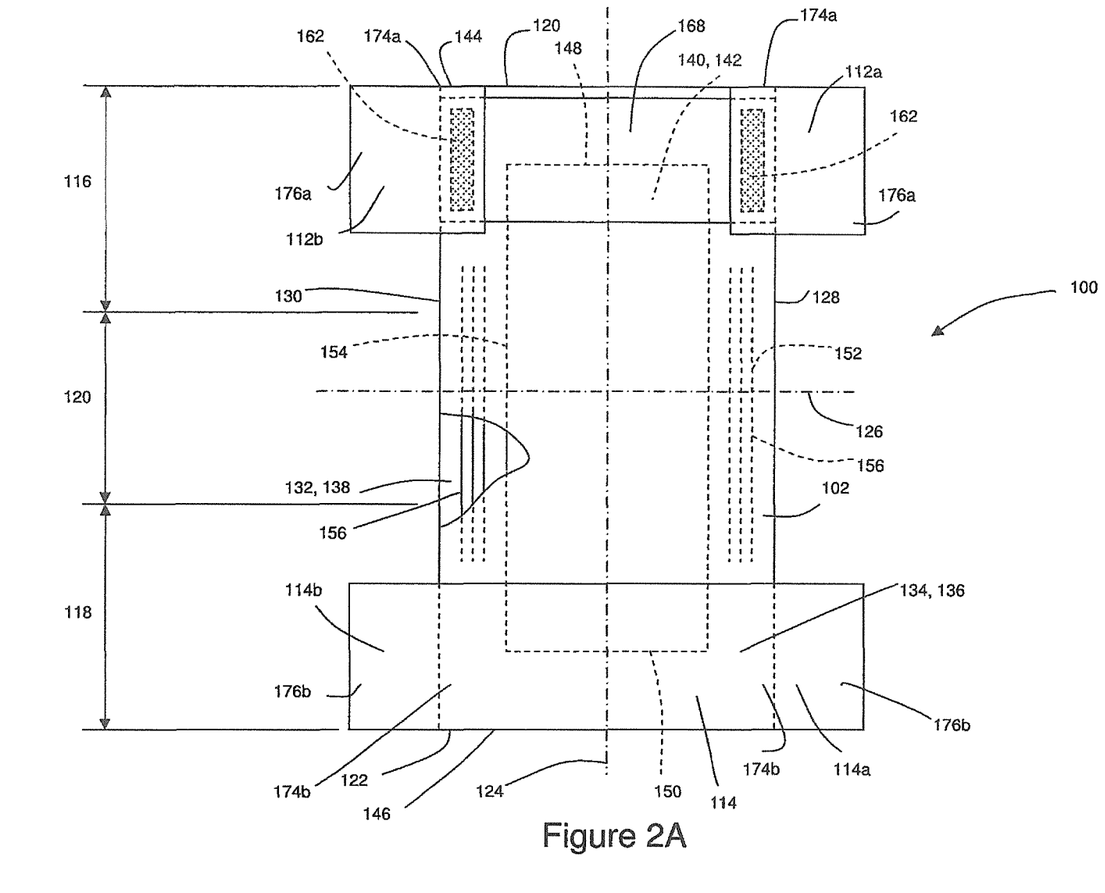
FIG. 2A is a partially cut away plan view of the diaper pant shown in FIG. 1.

FIGS. 1 and 2A show an example of a refastenable pant diaper 100 that may be constructed in accordance with the methods disclosed herein. In particular, FIG. 1 shows a perspective view of a refastenable pant diaper 100 in a pre-fastened configuration, and FIG. 2A shows a plan view of the pant diaper 100 with the portion of the diaper that faces away from a wearer oriented towards the viewer. The pant diaper 100 shown in FIGS. 1 and 2A includes a chassis 102, first front ear panels 112a, 112b, and second back ear panels 114a, 114b.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the pant diaper 100 may include an inner, body facing surface 132, and an outer, garment facing surface 134. The chassis 102 may include a backsheet 136 and a topsheet 138. An absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the front waist edge 120 and the back waist edge 122. The laterally extending end edges 144 and 146 of the chassis may form a portion of the laterally extending front waist edge 120 in the front waist region 116 and a portion of the longitudinally opposing and laterally extending back waist edge 122 in the back waist region 118. When the pant diaper 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the pant diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the pant diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the pant diaper 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper 100. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diapers 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 20090312730A1.

As mentioned above, pant diapers may be manufactured and provided to consumers in a configuration wherein the front waist region and the back waist region are pre-fastened or connected to each other as packaged, prior to being applied to the wearer. For example, the pant diaper 100 may be folded about a lateral centerline with the interior surface 132 of the first waist region 116 in surface to surface contact with the interior surface 132 of the second waist region 118. As such, pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

As previously mentioned, pant diapers may be configured with side panels connected with the chassis in one or both of the waist regions. For example, the pant diaper 100 shown in FIGS. 1 and 2A includes first side panels 112a, 112b connected with second side panels 114a, 114b, respectively. The first side panels 112a, 112b are refastenably connected with the chassis 102 in the first waist region 116 and extend laterally outward from the side edges 128, 130 of the chassis. The second side panels 114a, 114b are permanently connected with the chassis 102 in the second waist region 118 and extend laterally outward from the side edges 128, 130 of the chassis. As shown in FIG. 2A, the second side panels 114a, 114b are defined by opposing end regions of a continuous belt 114 that is permanently connected with the chassis 102 along the second waist region 118. The first side panel 112a is connected with the second side panel 114a, and the first side panel 112b is connected with the second side panel 114b. The first side panels 112a, 112b each include proximal regions 174a refastenably connected with the first waist region 116 of the chassis 102. And second ear panels 114a, 114b each include proximal regions 174b defined by the continuous belt 114 permanently connected with the second waist region 118 of the chassis 102. With reference to FIGS. 1 and 2A, a distal region 176a of the first side panel 112a and a distal region 176b of the second side panel 114a may be connected with each other along a first side seam 178. And a distal region 176a of the first side panel 112b and a distal region 176b of the second side panel 114b may be connected with each other along a second side seam 180.

Figure 2B:
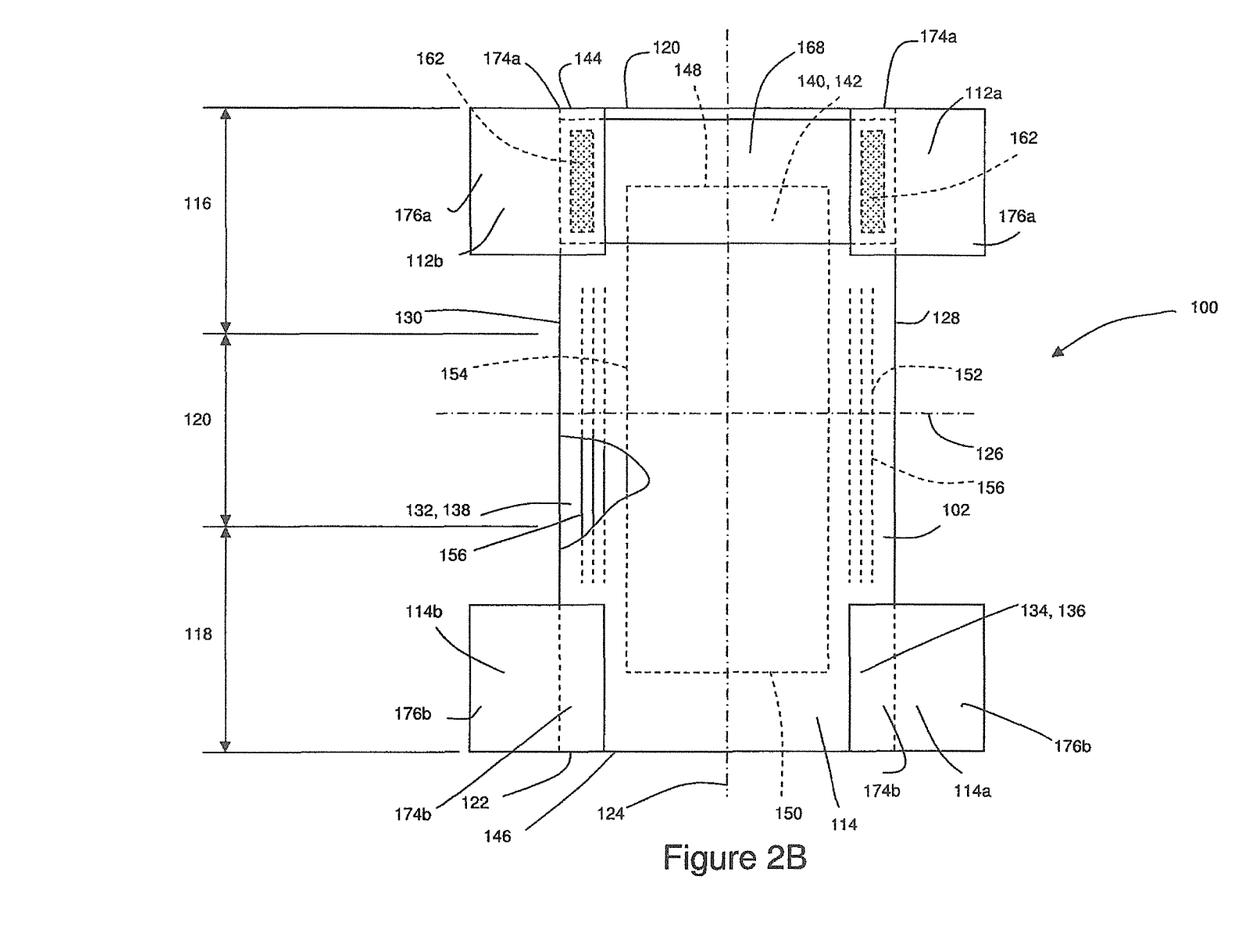
FIG. 2B is a partially cut away plan view of a second embodiment of a diaper pant.

It is to be appreciated that the second side panels may be configured in different ways other than as depicted in FIG. 2A. For example, FIG. 2B shows a plan view of a pant diaper 100 having the same components as described above with reference to FIG. 2A, except the second side panels 114a, 114b shown in FIG. 2B are not defined by opposing end regions of a continuous belt 114. Instead, the second side panels 114a, 114b shown in FIG. 2B are defined by two separate and discrete pieces of material connected with the second waist region 118 of the chassis 102. In particular, the second ear panels 114a, 114b each include proximal regions 174b permanently connected with the second waist region 118 of the chassis 102.

The side panels 112a, 112b and 114a, 114b may be substantially rectangular in shape or the side panels may be shaped in such a way as to provide an integral tab for ease of opening and refastening. The side panels may also be extensible in at least the lateral direction. The side panels may also be elastically extensible in the lateral direction. Furthermore, the side panels may be elastically extensible in both the longitudinal and lateral directions. The side panels may comprise a film, a nonwoven or a combination of film and nonwoven. The side panels may also comprise a plurality of strand-like filaments and a nonwoven. The strand-like elements may also be elastically extensible in at least the lateral direction.

It is to be appreciated that the side panels may include various types of materials, such as disclosed with respect to the elastic belts described in U.S. Pat. No. 7,569,039, which is hereby incorporated by reference herein. For example, the side panels may include plastic films; apertured plastic films; nonwoven or nonwoven webs of natural materials (e.g., wood or cotton fibers); synthetic fibers (e.g. polyolefins, polyamides, polyester, polyethylene, and/or polypropylene fibers); or combinations of natural and/or synthetic fibers; or coated woven or nonwoven webs. In some embodiment, the side panels may include a stretchable nonwoven. In other embodiments, the side panels may include an inner hydrophobic non-stretchable nonwoven material and an outer hydrophobic, non-stretchable nonwoven material. In addition, the side panels may include waist elastic material and side elastic material including one or more of elastic elements such as strand or panels extending in a transverse direction. The side panel elastic material may also be interposed between an outer layer and inner layer.

The ability to refasten an initially pre-fastened pant diaper may offer convenience to the caregiver. In some instances, it may be more convenient to apply the absorbent article like a traditional tape style diaper when away from home or when it is inconvenient to remove the clothing and/or shoes. Because it is difficult to predict when a change will be necessary and therefore when a particular mode of application will be needed, it is beneficial to have a disposable pant diaper that is adaptable to being applied either as a traditional tape style diaper or as a disposable pant diaper, pull-on. In addition, an absorbent article that can be applied like a traditional tape style diaper or a disposable pant diaper also permits inspection of the interior of the product without having to pull the product down. These refastenable structures may also provide dual functionality enabling the wrapping and disposal of the used product.

It is to be appreciated that the proximal regions of the side panels may be connected with the chassis in various ways, and the distal regions of the ear panels may be connected with each other in various ways. For example, the proximal regions and/or distal regions of the side panels disposed in one or both of the waist regions may be permanently bonded, releasably connected, and/or refastenably connected with the chassis and/or each other, with for example, adhesives, cohesives, thermal bonding, ultrasonic bonding, mechanical bonding and mechanical fastening e.g. hook and loop type fasteners. For example, one or more fastener elements may be located on the side panels and may be adapted to refastenably connect with one or more corresponding fastening elements located in the first or second waist regions or alternatively the fastener elements may be adapted to refastenably connect with one or more components of the absorbent article including the side panels. The diaper pants can also include other features such as elastically extensible side panels that may each include one or more pieces of material.

It should also be appreciated that the side panels in one waist region may have the same lateral extent from the side edge of the chassis to the distal edge of the side panel as the longitudinally opposed side panels in the opposite waist region or alternatively the side panels disposed in a first waist region may have different lateral extent as measured from the side edge of the chassis to the distal edge of the side panel than the side panels disposed in a second waist region.

As previously mentioned, the bonds of the side edge seams 178 and 180 may be permanent and can be formed in various ways appropriate for the specific materials employed. Thus, example bond types may include discrete bonds such as sonic sealed bonds, heat sealed bonds, high pressure bonds, radio frequency bonds, adhesive or cohesive bonds, sewed bonds, autogeneous bonds, and combinations thereof. In accordance with one aspect of the disclosure, the permanent side edge seams 178 and 180 may be joined by a predetermined pattern of heat/pressure or ultrasonic welds which withstands the forces and stresses exacted onto the side edge seam during application and wear of the pant. The permanent side edge seams 178, 180 may be formed as disclosed in U.S. Pat. Nos. 5,779,831; 5,772,825; 5,607,537; 5,622,589; 5,662,638; 6,042,673; and 6,726,792.

As mentioned above, the first side panels 112a, 112b may be refastenably connected with the first waist region 116 of the chassis 102. As such, the first side panels 112a, 112b may be configured to include fastening components 162, such as shown in FIG. 2A. The fastening components 162 may form a portion of or may be permanently bonded, adhered or otherwise joined directly or indirectly to the first side panels 112a, 112b at or adjacent the proximal edge regions 174a of the first side panels 112a, 112b. In some embodiments, the fastening components 162 may be permanently bonded to the first side panels 112a, 112b in various ways, such as for example, by adhesive bonds, sonic bonds, pressure bonds, thermal bonds or combinations thereof.

The fastening components 162 are adapted to refastenably connect with the first waist region 116 of the chassis 102. As such, the fastening components 162 may include various types of refastenably engageable fasteners and various types of refastenable fastening structures. For example, the fastening components 162 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphrodidic fasteners, and the like. Some examples of fastening systems and/or fastening components 162, 164 are discussed in U.S. Pat. Nos. 3,848,594; 4,662, 875; 4,846,815; 4,894,060; 4,946,527; 5,151,092; 5,221,274; 6,251,097; 6,669,618; 6,432,098; and U.S. Patent Publication Nos. 2007/0078427 and 2007/0093769.

As previously mentioned, the fastening components 162 may be adapted to refastenably engage or connect with another portion of the diaper 100. For example, as shown in FIG. 2A, the diaper 100 may include a connection zone 168, sometimes referred to as a landing zone, in the first waist region 116. As such, when the taped diaper 100 is placed on a wearer, the fasteners 162 are refastenably connected with the connection zone 168 in the first waist region 116 to form a closed waist circumference and a pair of laterally opposing leg openings. It is to be appreciated that the connection zone 162 may be constructed from a separate substrate that is connected with the chassis 102 of the taped diaper. In some embodiments, the connection zone may be integrally formed as part of the backsheet 136 of the diaper 100 or may be formed as part of the first and second ears in one or both of the waist regions, such as described in U.S. Pat. Nos. 5,735,840 and 5,928,212.

Figure 3:
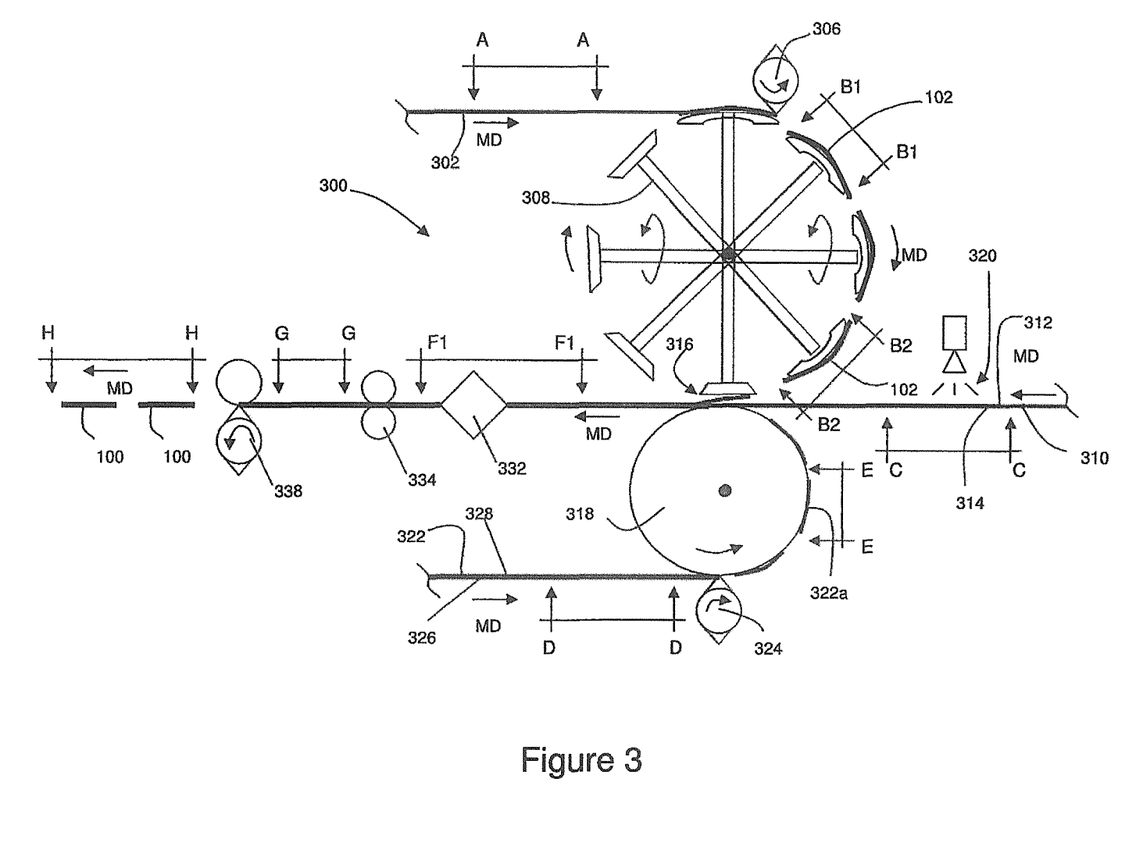
FIG. 3 is a schematic side view of a first converting apparatus adapted to manufacture pre-fastened, refastenable pant diapers.

As previously mentioned, the apparatuses and methods according to the present disclosure may be utilized to assemble various components of pre-fastened, refastenable pant diapers 100. For example, FIG. 3 shows a schematic view of a converting apparatus 300 adapted to manufacture pant diapers 100. The method of operation of the converting apparatus 300 may described with reference to the various components of pant diapers 100 described above and shown in FIGS. 1 and 2A.

As described in more detail below, the converting apparatus 300 shown in FIG. 3 operates to advance discrete chassis 102 along a machine direction MD such that the lateral axis of each chassis 102 is parallel with the machine direction, and wherein the chassis 102 are spaced apart from each other along the machine direction. In addition, the apparatus 300 refastenably connects the front side panels 112a, 112b with first waist regions 116 of advancing chassis 102 and permanently connects the back side panels 114a, 114b with the back waist regions 118 of advancing chassis 102.

Figures 5A, 5B, 5B:
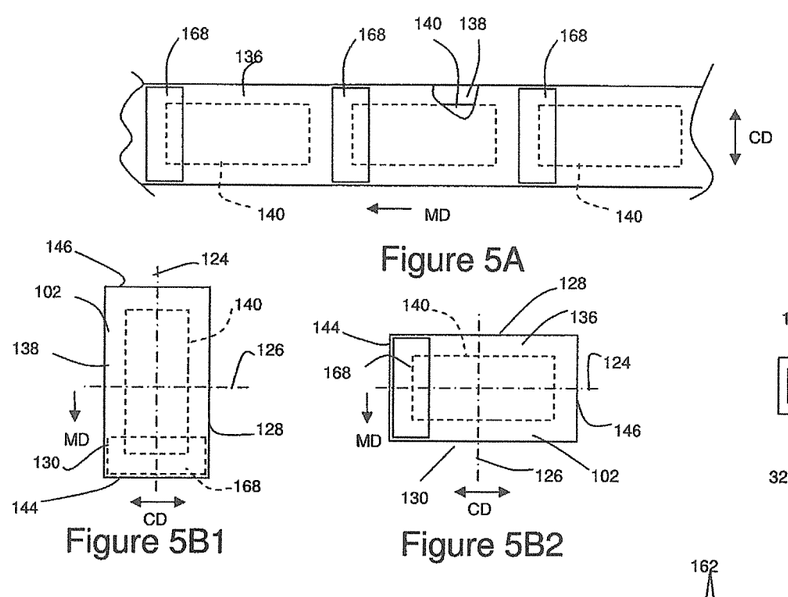

As shown in FIGS. 3 and 5A, a continuous length of chassis assemblies 302 are advanced in a machine direction MD to a carrier apparatus 308 and cut into discrete chassis 102 with knife roll 306. The continuous length of chassis assemblies may include absorbent assemblies 140 sandwiched between topsheet material 138 and backsheet material 136, leg elastics, barrier leg cuffs and the like. A portion of the chassis assembly is cut-away to show a portion of the topsheet material 138 and an absorbent assembly 140. The continuous length of chassis assemblies 302 may also include connection zones 168 connected with the backsheet material 136 and spaced apart from each other along the machine direction MD.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the first laterally extending end edge 144 as a leading edge and the second laterally extending end edge 146 as the trailing edge, it is to be appreciated that in other embodiments, the chassis 102 may be advanced in other orientations. For example, the chassis may be oriented such that the first laterally extending end edge 144 is a trailing edge and the second laterally extending end edge 146 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the first longitudinal side edge 128 as the trailing edge and the second longitudinal side edge 130 as the leading edge.

As discussed below with reference to FIGS. 3, 5C, 5D, 5E, 5F1, 5G, and 5H, the chassis 102 are transferred from the carrier apparatus 308 and combined with materials that form first side panels 112a, 112b and second side panels 114a, 114b.

Figure 5C:
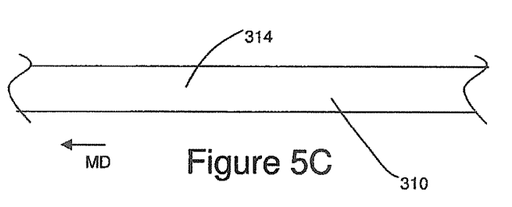
FIG. 5C is a view of a continuous length of advancing back side panel material from FIG. 3 taken along line C-C.

With reference to FIGS. 3 and 5C, the chassis 102 are transferred from the carrier apparatus 308 to a nip 316 between the carrier apparatus 308 and a carrier apparatus 318 where the chassis 102 is combined with a continuous length of advancing back side panel material 310. The back side panel material 310 defines a wearer facing surface 312 and an opposing garment facing surface 314. And the wear facing surface 312 of the back side panel material 310 may be combined with the garment facing surface 134 of the chassis 102 along the second waist region 116. As shown in FIG. 3, adhesive 320 may be intermittently applied to the wearer facing surface 312 before combining the back side panel material 310 with the discrete chassis 102.

Figure 5D:
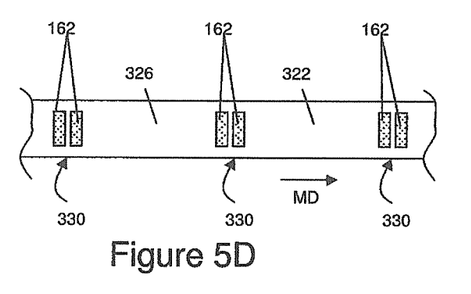
FIG. 5D is a view of a continuous length of front side panel material from FIGS. 3 and 4 taken along line D-D.
Figure 5E:
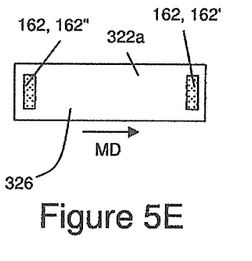
FIG. 5E is a view of a discrete length of front side panel material from FIGS. 3 and 4 taken along line E-E.

As shown in FIGS. 3, 5D, and 5E, a continuous length of front side panel material 322 advances in a machine direction MD to carrier apparatus 318, where a knife roll 324 cuts the continuous length of front side panel material 322 into discrete lengths of front side panel material 322a. As shown in FIG. 3, the discrete lengths of front panel material 322a are spaced from each other in the machine direction by the carrier apparatus 318. An example carrier apparatus 318 for achieving the spacing between discrete components is disclosed in disclosed in U.S. Pat. No. 7,587,966.

With continued reference to FIGS. 3 and 5D, the front side panel material 322 also defines a wearer facing surface 326 and an opposing garment facing surface 328. And fastening components 162 are intermittently spaced along the machine direction MD on the wearer facing surface 326 of the front side panel material 322. As shown in FIG. 5D, the fastening components 162 are arranged in pairs 330 of fastening components 162 in close proximity to each other, and the pairs 330 are spaced apart from other pairs 330 along the machine direction MD. With reference to FIGS. 3 and 5E, the knife 324 cuts the front side panel material 322 at locations between the two fastening components 162 of each pair 330, thus creating discrete lengths or patches of front side panel material 322a. As shown in FIG. 5E, fastening components 162 are located in opposing end portions each discrete length or patch of front side panel material 322a. As such, the discrete length of front side panel material 322a includes a leading end fastening component 162' and a trailing end fastening component 162". As shown in FIG. 3, the anvil roll 318 advances the discrete lengths of front side panel material 322a to the nip 316, where each discrete length of front side panel material 322a is connected with two chassis 102. More particularly, the leading end fastening component 162' is refastenably connected with the connection zone 168 in the first waist region 116 of a chassis 102 being transferred from the carrier apparatus 308 at the nip 316. And the trailing end fastening component 162" is refastenably connected with the connection zone 168 of a chassis 102 subsequently transferred from the carrier apparatus 308 at the nip 316. As such, opposing end portions of each discrete length of front side panel material 322a are refastenably connected with two chassis 102 traveling in the machine direction, such as shown in FIG. 5F1.

Figure 5F:
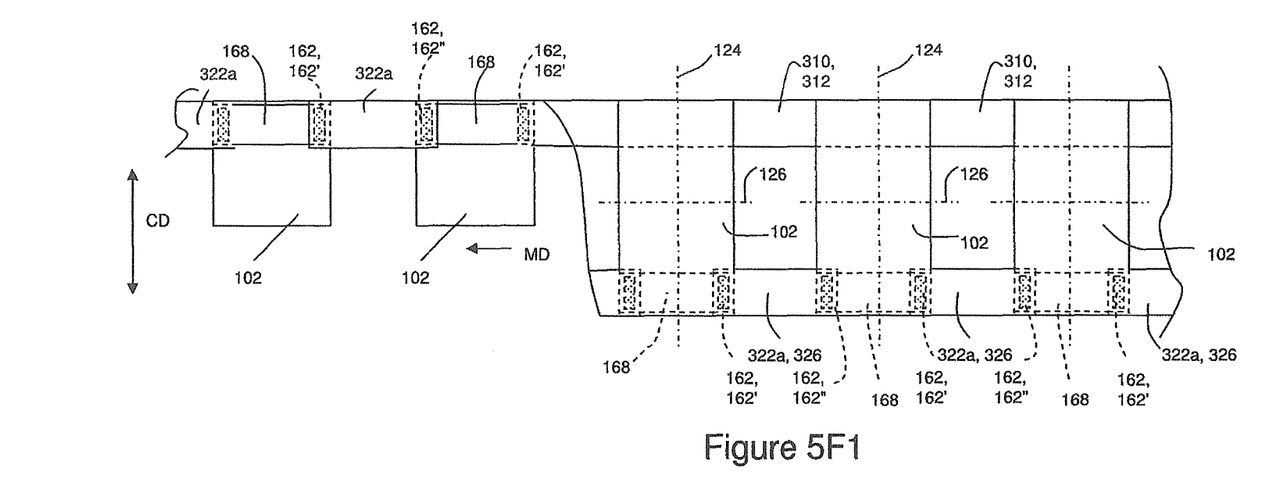
Figure 5F:
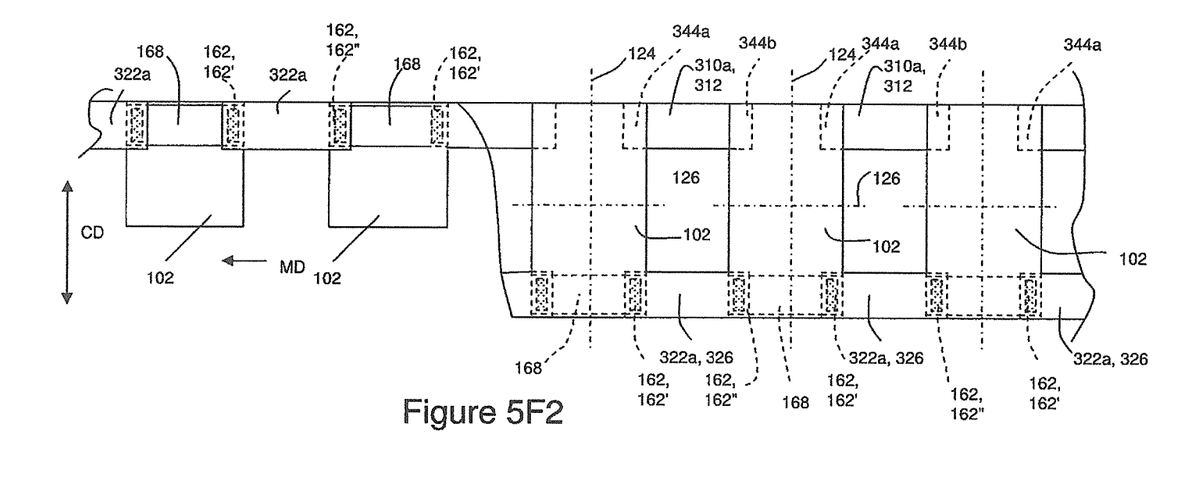
Figure 5G:
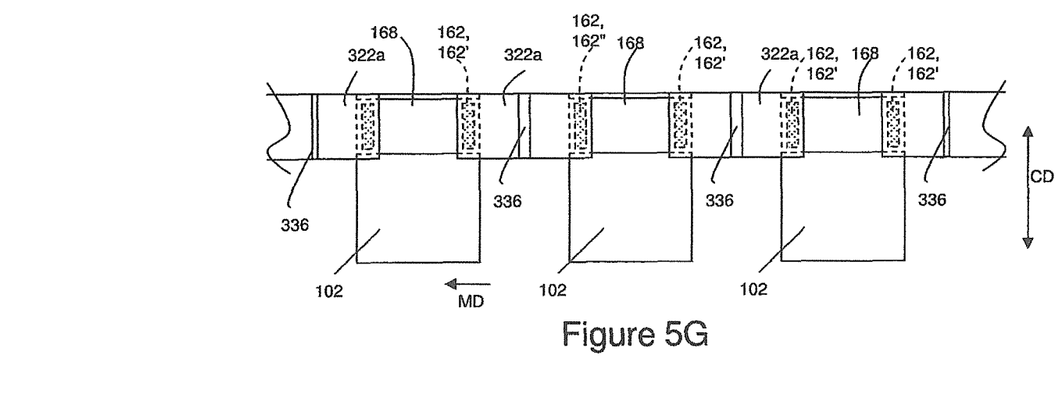
FIG. 5G is a view of the back side panel material bonded with a portion of the front side panel material from FIGS. 3 and 4 taken along line G-G.

With reference to FIGS. 3 and 5F1, multiple discrete chassis 102 spaced from each other along the machine direction MD are connected with each other by the back side panel material 310 and discrete lengths of front side panel material 322a. And the chassis 102 are advanced from the nip 316 to a folder 332. Various folder embodiments may be used, such as for example disclosed in U.S. Pat. No. 6,913,664, which is incorporated by reference herein. At the folder 332, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the back side panel material 310 extending between each chassis 102 in a facing relationship with the wearer facing surface 326 of the front side panel material 322a extending between each chassis 102. As shown in FIGS. 3 and 5G, the discrete chassis 102 connected with the back side panel material 310 and discrete lengths of front side panel material 322a are advanced from the folder 332 to a bonder 334. The bonder 334 operates to bond a portion of the back side panel material 310 extending between each chassis 102 with a portion of the front side panel material 322a extending between each chassis 102, thus creating discrete bond regions 336. It is to be appreciated that various types of bonders can be used to bond the back side panel material 310 with the front side panel material 322a, such as for example disclosed in U.S. Pat. Nos. 7,383,865 and 6,546,987, which are incorporated by reference herein.

Figure 5H:
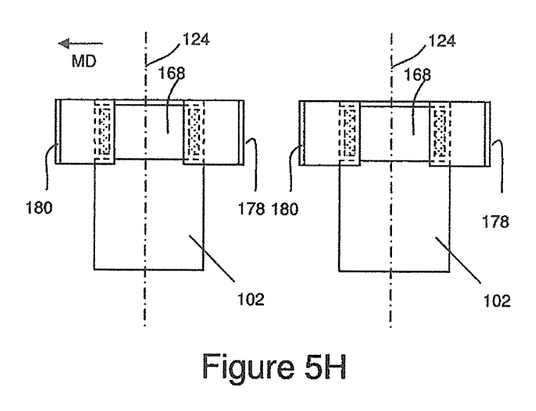
FIG. 5H is a view of two discrete absorbent articles advancing the machine direction MD from FIGS. 3 and 4 taken along line H-H.

As shown in FIGS. 3 and 5H, the discrete chassis 102 connected with the continuous back side panel material 310 and discrete lengths of front side panel material 322a are advanced from the bonder 334 to a knife roll 338 where the discrete bond regions 336 are cut into along the cross direction to create a first side seam 178 on an absorbent article 100 and a second side seam 180 on a subsequently advancing absorbent article.

Figure 4:
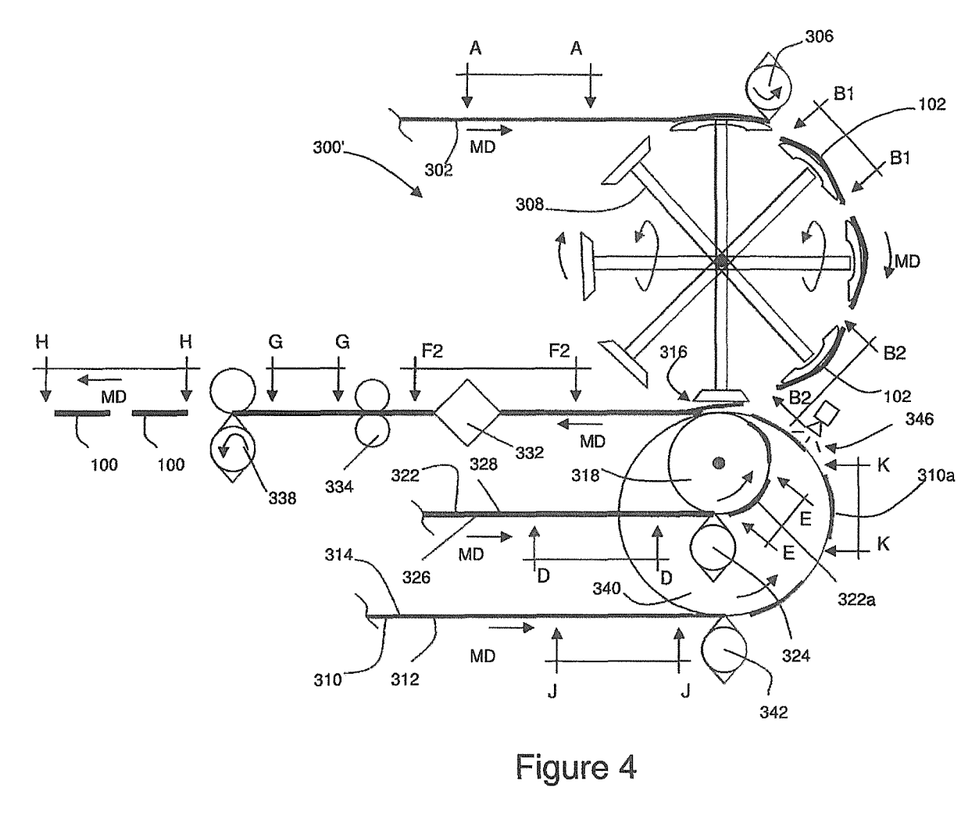
FIG. 4 is a schematic side view of a second converting apparatus adapted to manufacture pre-fastened, refastenable pant diapers.

FIG. 4 shows a schematic view of a second embodiment of a converting apparatus 300' adapted to manufacture pant diapers 100, such as shown in FIG. 2B. As discussed in more detail below, the method of operation of the converting apparatus 300' differs from the converting apparatus described above with respect to FIG. 3 with respect to the connection of two separate and discrete second ear panels 114a, 114b with the second waist region 118 of the chassis 102. Other aspects of the assembly process shown in FIG. 4 are the same as described above with reference to FIGS. 3, 5A, 5B1, 5B2, 5D, 5E, 5G, and 5H.

Figure 5J:
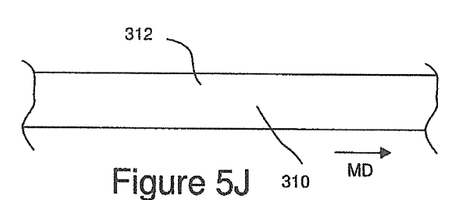
FIG. 5J is a view of a continuous length of advancing back side panel material from FIG. 4 taken along line J-J.
Figure 5K:
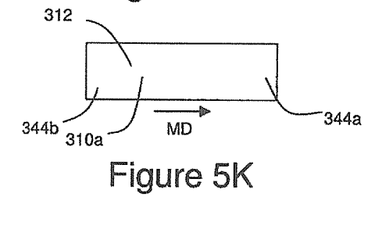
FIG. 5K is a view of a discrete length of advancing back side panel material from FIG. 4 taken along line K-K.

With reference to FIGS. 4 and 5J, a continuous length of back side panel material 310 defining a wearer facing surface 312 and an opposing garment facing surface 314 advances in a machine direction MD to a carrier apparatus 340. At carrier apparatus 340, a knife roll 342 cuts the continuous length of back side panel material 310 into discrete lengths of back side panel material 310a. As shown in FIG. 5K, each discrete length of back side panel material 310a includes a leading end portion 344a and a trailing end portion 344b. As shown in FIG. 3, the discrete lengths of back panel material 310a are spaced from each other in the machine direction by the carrier apparatus 340. An example carrier apparatus 340 for achieving the spacing between discrete components is disclosed in disclosed in U.S. Pat. No. 7,587,966. As shown in FIG. 3, adhesive 346 may be intermittently applied to the wearer facing surface 312 before combining the back side panel material 310a with the discrete chassis 102.

After applying adhesive, the wearer facing surface 312 of the back side panel material 310a may be connected with the garment facing surface 134 of the chassis 102 along the second waist region 116 at nip 316. More particularly, each discrete length of back side panel material 310a is connected with two chassis 102, wherein the leading end portion 346a is bonded with the second waist region 116 of a chassis 102 being transferred from the carrier apparatus 308 at the nip 316 and the trailing end portion 346b is bonded with the second waist region of another chassis 102 subsequently transferred from the carrier apparatus 308 at the nip 316. As such, opposing end portions of each discrete length of back side panel material 310a are bonded with two chassis 102 traveling in the machine direction, such as shown in FIG. 5F2. And the leading end portions 344a and the trailing end portions 344b of the back side panel material 310a correspond with the proximal regions 174b the second ear panels 114a, 114b discussed above with reference to FIG. 2B. From the nip 316, the discrete chassis connected with each other by the discrete lengths of back side panel material 310a and discrete lengths of front side panel material 322a are advanced from the nip 316 to folder 332, bonder 334, and knife roll 338 as discussed above with reference to FIGS. 5F1, 5G, and 5H.

Although the processes and apparatuses have been described in the context of assembling absorbent articles having side panels refastenably connected with the first waist region, it is to be appreciated that the processes and apparatuses described above can be configured to assemble absorbent articles having various other configurations. For example, the above described processes and apparatuses can be configured to assemble absorbent articles with side panels refastenably connected with the second waist region. In another example, the above described processes and apparatuses can be configured to assemble absorbent articles with four side panels refastenably connected to both the first and second waist regions, and wherein the corresponding side panels are bonded together along side seams.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for assembling disposable pre-fastened pant diapers, each pant diaper comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each pant diaper further comprising laterally opposed first side panels refastenably connected with the first waist region; and laterally opposed second side panels permanently connected with the second waist region and permanently connected with corresponding first side panels to form a waist opening, the process comprising the steps of:

advancing a first continuous web having a first surface and an opposing second surface in a machine direction wherein fastener components are connected with the first surface;

cutting the first continuous web into first discrete patches, each first patch having a leading end region, a trailing end region, and a central region disposed between the leading and trailing end regions, wherein a first fastener is located in the leading end region and a second fastener is located in the trailing end region;

advancing a second continuous web in the machine direction;

cutting the second continuous web into second discrete patches, each second patch having a leading end region, a trailing end region, and a central region disposed between the leading and trailing end regions, advancing a third continuous web in the machine direction;

cutting the third continuous web into discrete chassis, wherein each chassis advances such that the longitudinal axis is parallel with the machine direction;

turning each chassis such that the lateral axis is parallel with the machine direction;

refastenably connecting the first waist region of each chassis with a trailing end region of an advancing first patch and with a leading end region of a subsequently advancing first patch;

permanently connecting the second waist region of each chassis with a trailing end region of an advancing second patch and with a leading end region of a subsequently advancing second patch;

folding each chassis along the lateral axis to position the central region of each first patch into a facing relationship with the central region of each second patch;

bonding a portion of the central region of each first patch with a portion of each second patch to create discrete bond regions; and cutting the first and second patches along the bond regions to create discrete pre-fastened refastenable pant diapers.

2. The process of claim 1, wherein the first waist region is a front waist region.

3. The process of claim 1, wherein the second waist region is a back waist region.

4. The process of claim 1, wherein the first continuous web comprises a continuous length of front side panel material.

5. The process of claim 1, wherein the first patches comprise discrete lengths of front side panel material.

6. The process of claim 1, wherein the second continuous web comprises a continuous length of back side panel material.

7. The process of claim 1, wherein the second patches comprise discrete lengths of back side panel material.

8. The process of claim 1, wherein the third continuous web comprises a continuous length of chassis assemblies.

* * * * *